United States Patent [19]

Taheri

[11] Patent Number: 4,465,072
[45] Date of Patent: Aug. 14, 1984

[54] NEEDLE CATHETER

[76] Inventor: Syde A. Taheri, 268 Dan Troy Dr., Williamsville, N.Y. 14221

[21] Appl. No.: 468,076

[22] Filed: Feb. 22, 1983

[51] Int. Cl.³ .......................................... A61M 25/00
[52] U.S. Cl. ................................. 128/348.1; 128/756; 604/96
[58] Field of Search ................... 104/96, 103, 53, 165; 128/357, 756, 759, 348.1, 303 R

[56] References Cited

U.S. PATENT DOCUMENTS

| | | | |
|---|---|---|---|
| 2,701,559 | 2/1955 | Cooper | 604/103 X |
| 3,635,223 | 1/1972 | Klieman | 128/356 X |
| 3,664,328 | 5/1972 | Moyle, Jr. et al. | 128/756 |
| 3,833,003 | 9/1974 | Taricco | 604/53 |
| 3,996,938 | 12/1976 | Clark | 128/348.1 |

Primary Examiner—Stephen C. Pellegrino
Attorney, Agent, or Firm—Sommer & Sommer

[57] ABSTRACT

A needle catheter for scraping or thrombosing vascular walls has a sleeve mounted fast to a needle. The sleeve has a recess in which an inflatable balloon is mounted. The balloon may be selectively inflated and deflated by means of an extra-corporeal syringe. The balloon carries a plurality of abrasive burrs or ribs on the outer surface. After insertion, either subcutaneously or intravascularly, the balloon may be selectively inflated, after which the catheter may be moved longitudinally therealong to scrape or thrombose the walls of the vessel.

7 Claims, 4 Drawing Figures

NEEDLE CATHETER

BACKGROUND OF THE INVENTION

1. Field of the Invention

The present invention relates generally to the field of catheters, and more particularly to catheters used for scraping or thrombosing the interior or exterior walls of a blood vessel.

2. Description of the Prior Art

Many types of catheters are, of course, known. For example, U.S. Pat. No. 3,833,003 appears to disclose an intravascular catheter having an inflatable balloon at its forward end. However, this catheter did not have any abrasive burrs, with which a vascular vessel could be scraped or thrombosed, and its ballon was only inflated to temporarily occlude the vessel.

U.S. Pat. Nos. 4,332,254, 4,299,226 and 4,292,974 severally appear to disclose a balloon-type catheter used to dilate a vessel wall.

Finally, U.S. Pat. No. 2,927,584 discloses a surgical device having an inflatable balloon, the exterior surface of which is covered with a relatively soft fibrous flocking material (e.g., cotton flock, wool fiber, rayon acetate, nylon, dacron or similar synthetic fiber) to hold the device in position.

SUMMARY OF THE INVENTION

The invention provides an improved needle catheter, particularly adapted for intravascular or extravascular use, which comprises: a needle having a sharpened forward end; a sleeve mounted on the needle for movement therewith, the sleeve having a forward end arranged rearwardly of the needle forward end, having a distal rearward end, having an inner surface arranged to face the outer surface of the needle, and having an outer surface arranged to face away from the needle outer surface; an annular recess extending radially into the sleeve from its outer surface; a balloon mounted on the sleeve in the recess, the balloon having a plurality of abrasive burrs on its outwardly-facing surface, the balloon being selectively movable between a deflated position at which the balloon does not extend radially outwardly beyond the sleeve outer surface, and an inflated position at which the balloon does extend radially outwardly beyond the sleeve outer surface; passageway means forming a passageway along the sleeve, the passageway having one end communicating with the interior of the balloon, and having another end opening onto said sleeve outer surface proximate the distal end thereof; and pump means communicating with the interior of the balloon through the passageway and selectively operable to inflate and deflate the balloon; whereby, when the balloon is inflated, the inventive catheter may be used to scrape or thrombose the interior or exterior wall of a blood vessel.

Accordingly, the general object of the invention is to provide an improved needle catheter.

Another object is to provide a needle catheter which may be used to scrape or thrombose the interior or exterior walls of a blood vessel.

Another object is to provide a catheter for post-surgical treatment of varicose vein patients.

These and other objects and advantages will become apparent from the foregoing and ongoing specification, the drawings, and the appended claims.

DESCRIPTION OF THE PREFERRED EMBODIMENTS

Figure 1:
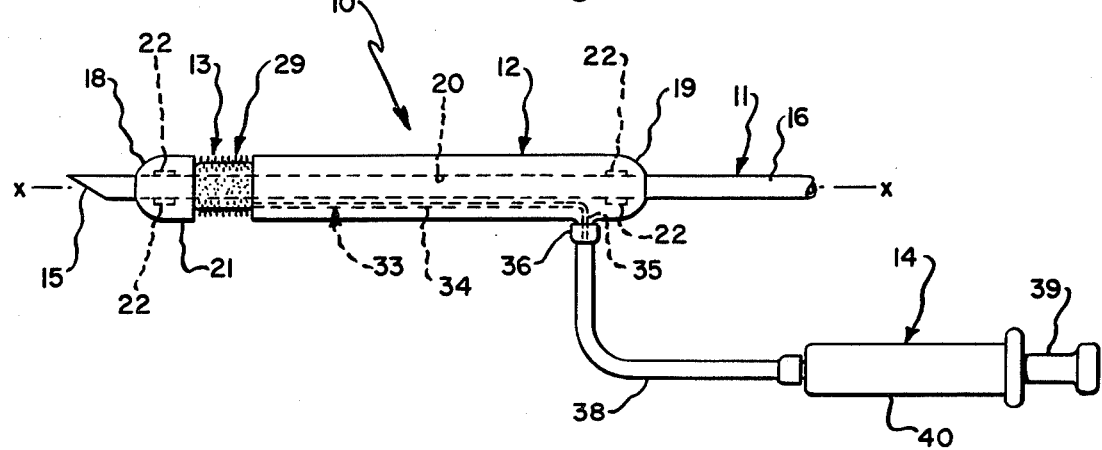
FIG. 1 is a fragmentary side elevation of the improved needle catheter, with the balloon deflated.

At the outset, it should be clearly understood that like reference numerals are intended to identify the same elements and/or structure consistently throughout the several drawing figures, as such elements and/or structure may be further described or explained by the entire written specification of which this detailed description is an integral part.

Referring now to the drawings, and more particularly to FIG. 1 thereof, the invention provides an improved needle catheter, of which the presently preferred embodiment is generally indicated at 10.

The improved catheter 10 is shown as broadly including a needle 11, a sleeve 12, a balloon 13, and a syringe 14.

The needle 11 is shown as being a horizontally-elongated rod-like member having its leftward forward end sharpened, as indicated at 15. Rearwardly of its sharpened forward end, the outer surface 16 of the needle is, of course, cylindrical. The needle may be 22-16 gauge in diameter, and about 6 inches long.

The sleeve 12 is a horizontally-elongated somewhat-tubular member mounted fast to an intermediate portion of the needle. Sleeve 12 has a leftward forward end 18 and a rightward rear end 19, both of these ends being arcuate and preferably spherical. The sleeve has an inner cylindrical surface 20 arranged to face, and preferably contact, the needle outer surface 16; and has an outer cylindrical surface 21 arranged to face away from needle surface 16. Hence each of surfaces 16, 20 and 21 is generated about the horizontal needle axis, this being indicated at x—x in FIG. 1. The sleeve is mounted on the needle against either axial or rotative movement relative thereto. In the preferred embodiment, one or more keys 22, severally extending outwardly from the needle outer surface 16, is received in a corresponding number of cooperatively-configured keyways 23 provided in the sleeve, to prevent such undesired relative rotative movement therebetween. Four such key-keyway connections are shown in FIG. 1.

An annular recess, generally indicated at 24, is shown as extending into the sleeve from its outer surface 21. This recess, which is positioned just rearwardly of forward end 18, is bounded by a rearwardly-facing annular vertical surface 25, an outwardly-facing coaxial cylindrical surface 26, and a forwardly-facing annular vertical surface 28.

Figure 2:
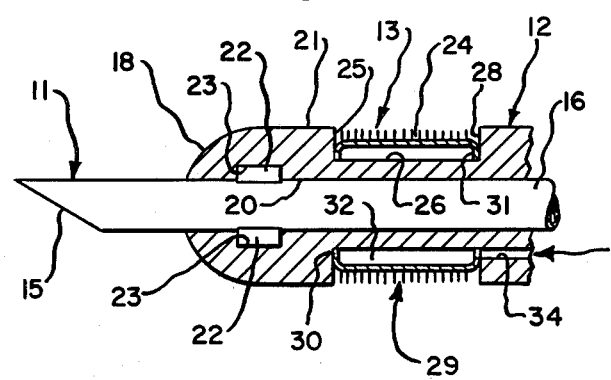
FIG. 2 is a fragmentary enlarged detail view of the forward end of the needle catheter.
Figure 3:
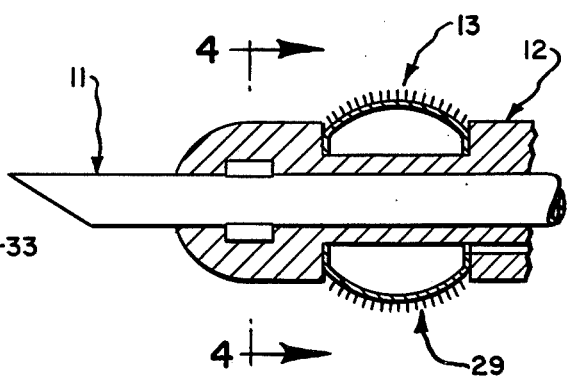
FIG. 3 is a view similar to FIG. 2, but showing the balloon as having been inflated.
Figure 4:
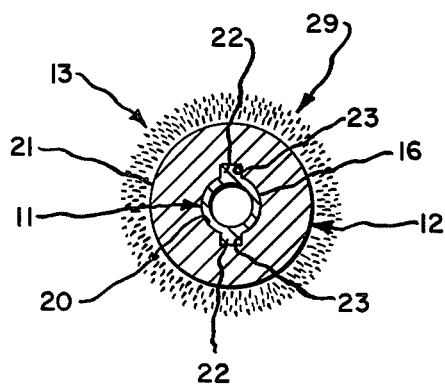
FIG. 4 is a fragmentary transverse vertical sectional view of the needle catheter, this view being taken generally on line 4—4 of FIG. 3.

An annular balloon, generally indicated at 29, is arranged within the recess. This balloon has an in-turned forward marginal end portion 30 glued or otherwise secured to sleeve recess surface 25, and has an in-turned rearward marginal end portion 31 similarly glued or otherwise secured to recess surface 28. This balloon is therefore mounted on the sleeve in the recess to form therebetween an annular sealed chamber 32. Fluid may be selectively supplied to, or withdrawn from, chamber 32 to either inflate (FIG. 3) or deflate (FIG. 2) the balloon. When deflated (FIG. 2), the balloon is contained within recess 24, and no part of the balloon extends outwardly beyond sleeve outer surface 21. However, when inflated (FIG. 3), the portions of the balloon do extend outwardly beyond sleeve surface 21. The balloon is also shown as carrying a plurality of outwardly-extending abrasive burr-like pips or ribs on its outer surface. If desired, the balloon may be made of silastic, and the pips or ribs may be silastic, silicone or some other suitable material.

The sleeve is shown as being further provided with an internal passageway, generally indicated at 33, which includes a horizontally-elongated hole 34 and an intersecting radial hole 35. The forward end of hole 34 communicates with balloon chamber 32, while its rearward end is intersected by the innermost end of radial hole 35 (FIG. 1). The outermost end of hole 35 penetrates a nipple 36 extending radially outwardly from sleeve outer surface 21 proximate its rearward end.

A flexible conduit or hose 38 has one end mounted on sleeve nipple 36, and has its other end mounted on another nipple of syringe 14. Persons skilled in this art will appreciate that syringe 14 is basically a manually-operable piston-and-cylinder. Because it communicates with balloon chamber 32, the syringe piston 39 may be moved in the appropriate direction relative to its cylinder 40 to selectively inflate or deflate the balloon.

Of course, passageway 33 is only one specific example. Such passageway might be alternatively provided between the needle and sleeve. Hence, in the claims, the expression "passageway means" is intended to generally refer to these specific passageways, and their functional equivalents. Similarly, a syringe is only one mechanism, albeit conveniently available in a medical environment for selectively inflating and deflating the balloon. If desired, other types of pumps and air handling devices might be substituted therefore. Hence, in the claims, the expression "pump means" is intended to generally cover these specific embodiments, and their functional equivalents.

The improved needle catheter is deemed to be particularly useful in the treatment of varicose veins, and particularly in the post-surgical scraping or thrombosing of same. The catheter, with its balloon initially deflated may be either inserted into a blood vessel, or inserted subcutaneously to a circumvascular position. Once in position, the syringe may be operated to inflate the balloon to the extent desired. Thereafter, the catheter may be translated longitudinally along the vessel to scrape or thrombose the same. Of course, the syringe may be reversely operated to deflate the balloon, after which the catheter may be removed.

Therefore, while the preferred embodiment of the inventive needle catheter has been shown and described, and several modifications thereof discussed, persons skilled in this art will readily appreciate that various additional changes and modifications may be made without departing from the spirt of the invention, as defined and differentiated by the following claims.

What is claimed is:

1. A needle catheter, comprising:
   a needle having a sharpened forward end;
   a sleeve mounted on the needle for movement therewith, said sleeve having a forward end arranged rearwardly of said needle forward end, having a distal rearward end, having an inner surface arranged to face the outer surface of said needle, and having an outer surface arranged to face away from said needle outer surface;
   a key-keyway connection between said needle and sleeve to prevent relative rotation therebetween;
   an annular recess extending radially into said sleeve from said outer surface;
   a balloon mounted on said sleeve in said recess, said balloon having a plurality of abrasive burrs on its outwardly-facing surface, said balloon being movable between a deflated position at which said balloon does not extend radially outwardly beyond said sleeve outer surface, and an inflated position at which said balloon does extend radially outwardly beyond said sleeve outer surface;
   passageway means forming a passageway along said sleeve, said passageway having one end communicating with the interior of said balloon, and having another end opening onto said sleeve outer surface proximate said distal end thereof; and pump means communicating with the interior of said balloon through said passageway, and selectively operable to inflate and deflate said balloon.

2. A needle catheter as set forth in claim 1 wherein said sleeve is non-axially and non-rotatably mounted on said needle.

3. A needle catheter as set forth in claim 1 wherein said sleeve is mounted fast to said needle.

4. A needle catheter as set forth in claim 1 wherein said needle forward end is arcuate.

5. A needle catheter as set forth in claim 1 wherein said passageway means is provided completely in said sleeve.

6. A needle catheter as set forth in claim 1 wherein said passageway is provided, for at least a portion of its longitudinal extent, between said sleeve and needle.

7. A needle catheter as set forth in claim 1 wherein said pump means is a syringe.

* * * * *